United States Patent [19]

Wrobleski

[11] Patent Number: 4,515,973

[45] Date of Patent: May 7, 1985

[54] PROCESS FOR PRODUCING MALEIC ANHYDRIDE

[75] Inventor: James T. Wrobleski, St. Louis, Mo.

[73] Assignee: Monsanto Company, St. Louis, Mo.

[21] Appl. No.: 566,378

[22] Filed: Dec. 28, 1983

[51] Int. Cl.$^3$ ............................................ C07D 307/60
[52] U.S. Cl. ...................................... 549/259; 502/209
[58] Field of Search ........................ 549/259; 502/209

[56] References Cited

U.S. PATENT DOCUMENTS 3,293,268  12/1966  Bergman et al. ..................... 549/259
4,085,122   4/1978  Stefani et al. ....................... 549/259
4,100,106   7/1978  Stefani et al. ....................... 502/509

OTHER PUBLICATIONS

Malowan, Inorganic Synthesis, vol. III, Editor, L. Audrieth, McGraw-Hill, N.Y., (1950), pp. 96–98.

*Primary Examiner*—Henry R. Jiles
*Assistant Examiner*—Bernard I. Dentz
*Attorney, Agent, or Firm*—W. W. Brooks; J. C. Logomasini; A. H. Cole

[57] ABSTRACT

Maleic anhydride is produced by the oxidation of a nonaromatic hydrocarbon having at least four carbon atoms in a straight chain with molecular oxygen or a molecular oxygen-containing gas in the vapor phase in the presence of a phosphorus-vanadium mixed oxide catalyst. Such catalysts are prepared by contacting a tetravalent vanadium compound, dissolved in an aqueous, non-oxidizing acid medium, with crystalline diphosphoric acid to form a phosphorus-vanadium mixed oxide catalyst precursor. The resulting catalyst precursor-containing solution is subjected to a series of concentration/dilution cycles to induce crystallization of the catalyst precursor. The crystals are collected, dried, formed into desired structures, and calcined at temperatures from about 300° C. to about 600° C.

26 Claims, No Drawings

PROCESS FOR PRODUCING MALEIC ANHYDRIDE

BACKGROUND OF THE INVENTION

1. Field of the Invention

This invention relates to a process for the production of maleic anhydride by the oxidation of nonaromatic hydrocarbons. More particularly, this invention is directed to a process for the partial oxidation of nonaromatic hydrocarbons in the vapor phase with molecular oxygen or a molecular oxygen-containing gas to produce maleic anhydride in excellent yields.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these varied needs.

2. Description of the Prior Art

The preparation of phosphorus-vanadium mixed oxides and their use as catalysts in the production of maleic anhydride is known. As an example, U.S. Pat. No. 4,085,122 discloses a process which involves a salt of tetravalent vanadium, dissolved in an aqueous, non-oxidizing acid solution, with orthophosphoric acid. After the solution is concentrated, the vanadium salt complex is pre-cipitated by adding water. The precipitate is collected, dried, formed into the desired form, and subjected to a heat treatment of at least 300° C. to produce the catalyst. The resulting catalyst is concontacted with a $C_4$ hydrocarbon, n-butane being preferred, in the vapor phase at a temperature between 320° C. and 500° C. to yield maleci anhydride.

U.S. Pat. No. 3,293,268 teaches a process of oxidizing saturated aliphatic hydrocarbons to maleic anhydride under controlled temperature conditions in the presence of a phosphorus-vanadium mixed oxide catalyst produced in a specified manner.

Although these prior art processes generally produce the desired maleic anhydride product, the commercial utility of a catalytic process is highly dependent upon the cost of the catalyst employed, the conversion of the reactant(s), and the yield of the desired product(s). In many instances, a reduction in the costs of a catalyst system employed in a given process on the order of a few cents per kilogram or pound, or a small percent increase in the yield of the desired product represents a tremendous commercial economical savings and advantage. Accordingly, research efforts are continually being made to define new or improved catalyst systems and methods and process of making new and old catalyst systems to reduce the costs and/or upgrade the activity and selectivity of such catalyst systems in such processes. The discovery of the process of the instant invention, therefore, is believed to be a decided advance in the art.

SUMMARY OF THE INVENTION

It is an object of this invention to provide a process for the oxidation of nonaromatic hydrocarbons to produce maleic anhydride.

Another object of this invention is to provide a process for the production of maleic anhydride in excellent yields.

These and other objects, aspects, and advantages of this invention will become apparent to those skilled in the art from the accompanying description and claims.

The above objects are achieved by the process disclosed herein for the production of maleic anhydride by the oxidation of a nonaromatic hydrocarbon having at least four carbon atoms in a straight chain with molecular oxygen or a molecular oxygen-containing gas in the vapor phase at a temperature from about 300° C. to about 600° C. in the presence of a phosphorus-vanadium mixed oxide catalyst, wherein the catalyst is prepared by:

(a) contacting a tetravalent vanadium compound, dissolved in an aqueous, non-oxidizing acid medium, with crystalline diphosphoric acid to form a phosphorus-vanadium mixed oxide catalyst precursor;

(b) crystallizing the catalyst precursor from the catalyst precursor aqueous solution in a controlled manner involving at least three cycles of concentrating/diluting wherein a fraction of the liquid from about 0.15 to about 0.85 is removed during the concentrating step and water is added during the diluting step in an amount sufficient to provide a water added/solvent removed volume ratio from about 0.10 to about 10.0, with the proviso that the final liquid/initial liquid volume ratio is from about 0.20 to about 2.0;

(c) recovering the catalyst precursor crystals;

(d) drying the catalyst precursor;

(e) forming the dried catalyst precursor into structures; and (f) calcining the catalyst precursor structures at a temperature from about 300° C. to about 600° C.

DETAILED DESCRIPTION OF THE INVENTION

In accordance with this invention, a process is provided for the production of maleic anhydride by the oxidation of a nonaromatic hydrocarbon having at least four carbon atoms in a straight chain with molecular oxygen or a molecular oxygen-containing gas in the vapor phase at a temperature from about 300° C. in the presence of phosphorus-vanadium mixed oxide catalysts. Broadly described, the catalysts employed in the instant process comprises contacting a tetravalent vanadium compound, dissolved in an aqueous, non-oxidizing acid medium, with crystalline diphosphoric acid to form a phosphorus-vanadium mixed oxide catalyst precursor, crystallizing the catalyst precursor, recovering the catalyst precursor, forming the catalyst precursor into structures, and calcining the structured catalyst precursor to form the catalyst.

For purposes of this invention, the term "yield" means the ratio of the moles of maleic anhydride obtained to the moles of hydrocarbon feedstock introduced into the reactor. The term "selectivity" means the ratio of moles of maleic anhydride obtained to the moles of hydrocarbon feedstock reacted or converted. The term "conversion" means the number of moles of hydrocarbon feedstock reacted to the moles of hydrocarbon introduced into the reactor. The term "gas hourly space velocity" or "GHSV" or simply "space velocity" means the hourly volume of gaseous feed expressed in cubic centimeters (cc) at room temperature (20° C.) and atmospheric pressure, divided by the catalyst bulk volume, expressed in cubic centimeters, the term expressed as cc/cc/hour or $hr^{-1}$.

The tetravalent vanadium compounds suitable for use as a source of vanadium in the catalysts employed in the process of the instant invention are those tetravalent compounds known to the art. The tetravalent vanadium can be obtained either by the use of a tetravalent vanadium compound or, alternatively, by the use of an easily accessible pentavalent vanadium compound, such as vanadium pentoxide, which is reduced in situ to a tetravalent vanadium compound. Examples of suitable tetravalent vanadium compounds are vanadium tetrachloride ($VCl_4$); vanadium dioxide ($VO_2$), sometimes termed vanadium tetroxide ($V_2O_4$); vanadium oxydibromide ($VOBr_2$); and vanadium oxydichloride ($VOCl_2$), which is the preferred compound. In general, the tetravalent vanadium compounds suitable for use in the instant process are halides, oxides, and oxyhalides of vanadium. Examples of useful pentavalent vanadium compounds, which can be reduced in situ to obtain a tetravalent vanadium compound are vanadium pentoxide ($V_2O_5$), which is the preferred compound; vanadium oxytribromide ($VOBr_3$); vanadium oxytrichloride ($VOCl_3$); and vanadium pentachloride ($VCl_5$).

Crystalline diphosphoric acid, also known as pyrophosphoric acid, $H_4P_2O_7$, is employed as the source of (pentavalent) phosphorus in the catalysts employed in the instant process. Crystalline (or solid) diphosphoric acid is obtainable by procedures well known to those skilled in the art. In general, crystalline diphosphoric acid is obtained by the spontaneous crystallization of a polyphosphoric acid mixture containing $79.8\pm0.2\%$ phosphorus pentoxide ($P_2O_5$). Such a liquid polyphosphoric acid may be prepared by (1) dehydration of 85% orthophosphoric acid, (2) dissolving $P_2O_5$ in 85% orthophosphoric acid, (3) adding water to commercial "tetraphosphoric acid," or (4) allowing $POCl_3$ to react with 85% orthophosphoric acid. For additional information regarding the preparation of crystalline diphosphoric acid, see Malowan, *Inorganic Synthesis.* Audrieth, Ed., Vol. III, pp. 96-98, McGraw Hill, New York, N.Y. 1950, which is herein incorporated by reference.

To prepare precursors to the catalysts employed in the instant process, a suitable vanadium compound dissolved in an aqueous, non-oxidizing acid medium is contacted with crystalline diphosphoric acid and heated to induce complete solution and form the desired catalyst precursor.

When a pentavalent vanadium compound, such as $V_2O_5$, is employed as the starting material, it must be reduced to the tetravalent valence state. The desired reduction is readily accomplished by contacting the pentavalent vanadium compound with a suitable reducing agent in an acid medium. As is well known to those skilled in the art, hydrohalic acids or oxalic acid solutions, which are mild reducing agents, can serve not only as the acid but also as the reducing agent for the pentavalanet vanadium. Among these compounds, hydrochloric acid is preferred.

The atom ratio of phosphorus to vanadium in the starting material is important since it controls, in part, the phosphorus/vanadium (P/V) atom ratio in the final catalyst. The catalysts employed in the process of the instant invention exhibit a P/V atom ratio from about 0.5 to about 2.0, with a P/V atom ratio of about 0.95 to about 1.2 being preferred. As previously noted, the atom ratio in the catalyst is determined, in part, by the P/V atom ratio in the starting material as charged to the reactor. However, since the catalyst precursor is normally recovered by filtration or centrifugation and decantation, the analyzed P/V atom ratio is usually slightly less than the corresponding charged ratio. Typically, a P/V (charge) atom ratio of about 1.0 yields a catalyst having a phosphorus/vanadium (analyzed) atom ratio of about 0.95, while a charged atom ratio of about 1.2 yields a catalyst precursor (and catalyst) having an analyzed atom ratio of about 1.0, thus indicating that a portion of the charged phosphorus relative to the charged vanadium is lost during the recovery step.

After the phosphorus-vanadium mixed oxide catalyst precursors have been formed by heating the tetravalent vanadium compound and the diphosphoric acid, it is necessary to recover the catalyst precursors. Numerous prior art techniques for recovering catalyst precursors from solution are well known to those skilled in the art. However, such prior art techniques—evaporating to dryness and rapid or uncontrolled precipitation or crystallization, for example—are unsatisfactory for use in preparing the catalysts employed in the instant process in that the resulting catalysts exhibit none of the advantages characteristic of the catalysts prepared as desribed herein. Thus, the catalyst precursor is crystallized from the aqueous solution by a controlled crystallization technique. The technique involves at least three cycles of concentrating/diluting (or distillation/water addition) of the catalyst precursor aqueous solution (mixture). In each cycle, a fraction of the solvent (liquid) ranging from 0.15 to about 0.85 is removed during the concentrating step and water is added in an amount sufficient to provide a water added/solvent removed volume ratio from about 0.10 to about 10.0. The final liquid/initial liquid (after formation of the catalyst precursor) volume ratio, however, should range from about 0.20 to about 2.0. Within this range, the amount of liquid present is sufficiently small to minimize the retention of catalyst precursor crystals in solution while at the same time sufficiently large to facilitate ease of separating the catalyst precursor crystals from the supernatant liquid. Separation or recovery of the catalyst precursor crystals is readily accomplished by filtration, centrifugation and decantation, and the like.

The maximum number of concentration/diluting cycles is not narrowly critical. All that is necessary is that at least three of such cycles are performed and that crystallization has occurred to an extent sufficient to provide a substantial amount of crystalline catalyst precursor. In general, however, little, if any, advantage is observed beyond a maximum of six cycles.

The theory of the controlled crystallization is not completely understood. However, it is believed that the concentration/dilution cycles cause repetitive crystallizations/dissolutions of the catalyst precursor. This, in turn, results in the formation of crystals which are smaller and more uniform than crystals obtained from prior art procedures, such as evaporation to dryness.

After the catalyst precursors have been recovered from the solution, they are then formed into structures suitable for use in a maleic anhydride reactor. Techniques for forming appropriate structures from the catalyst precursors for use in a fluidized bed reactor or in a fixed bed, heat exchanger type reactor are well known to those skilled in the art. For example, the catalyst precursors can be comminuted for use in a fluidized bed reactor. Similarly, the catalyst precursors can be structured for use in a fixed bed, heat exchanger type reactor by prilling or tableting the precursors.

After the catalyst precursors have been formed into the desired structures, they can be calcined in a molecular oxygen-containing atmosphere, such as air, at temperatures from about 300° C. to about 600° C. for a suitable period of time, usually at least two hours, to convert the catalyst precursors to the active catalyst.

The exact calcination conditions employed are not narrowly critical. All that is necessary is that the catalyst precursors be calcined until about 15 atom percent to about 90 atom percent of the vanadium has been converted to pentavalent vanadium. If more than about 90 atom percent of the vanadium is oxidized to pentavalent vanadium, usually caused by calcining too long, or at too high a temperature, the selectivity of the resultant catalyst and the yield of maleic anhydride decrease markedly. On the other hand, oxidation of less than about 15 atom percent of the vanadium during the calcination does not seem to provide a catalyst having sufficient activity to convert suitable nonaromatic hydrocarbon feedstocks to maleic anhydride at a reasonable rate. In general, calcination at temperatures from about 400° C. to about 500° C. for a period of time from about four hours to about eight hours, usually six hours, is sufficient.

The phosphorus-vanadium mixed oxide catalysts can be used (in a suitable reactor) to convert nonaromatic hydrocarbons to maleic anhydride. A mixture of hydrocarbon and a molecular oxygen-containing gas, (including molecular oxygen), such as air, can be contacted with the catalyst at temperatures between about 300° C. and 600° C. at concentrations of from about one mole percent to about 10 mole percent hydrocarbon at a gas hourly space velocity (GHSV), or simply space velocity, up to about 4,000 hr$^{-1}$ to produce maleic anhydride. However, the initial yield of maleic anhydride may be low; and if this is the case, the catalyst, as will occur to those skilled in the art, can be "conditioned" by contacting the catalyst with low concentrations of hydrocarbon and molecular oxygen-containing gas at low space velocities for a period of time before production operations begin.

The catalysts employed in process of the instant invention are useful in a variety of reactors to convert nonaromatic hydrocarbons to maleic anhydride. The catalyst may be used in a fixed bed reactor using tablets, pellets, or the like, or in a fluidized bed reactor using catalysts preferably having a particle size of less than about 300 microns. Details of the operation of such reactors are well known to those skilled in the art.

The reaction to convert nonaromatic hydrocarbons to maleic anhydride requires only contacting the hydrocarbon admixed with a molecular oxygen-containing gas, such as air or molecular oxygen enriched air, with the catalyst at elevated temperatures. In addition to the hydrocarbon and molecular oxygen, other gases, such as nitrogen or steam, may be present or added to the reactant feedstream. Typically, the hydrocarbon is admixed with the molecular oxygen-containing gas, preferably air, at a concentration of about one mole percent to about 10 mole percent hydrocarbon and contacted with the catalyst at a space velocity of about 100 hr$^{-1}$ to about 4,000 hr$^{-1}$ at a (bath) temperature from about 300° C. to about 600° C., preferably about 1450 hr$^{-1}$ and about 325° C. to about 425° C., to provide an excellent selectivity to and yield of maleic anhydride.

The catalyst prepared in accordance with the instant process are particularly useful in fixed bed (tube), heat exchanger type reactors. The tubes of such reactors can vary in diameter from about 0.635 cm (0.25 inch) to about 3.81 cm (1.5 inches) and the length can vary from about 15.24 cm (6 inches) to about 304.8 cm (10 feet) or more. It is desirable to have the surfaces of the reactors at relatively constant temperatures, and some medium to conduct heat from the reactors is necessary to aid temperature control. Non-limiting examples of such media include Woods metal, molten sulfur, mercury, molten lead, and eutectic salt baths. A metal block reactor whereby the metal surrounding the tube acts as a temperature regulating body can also be used. The reactor or reactors can be constructed or iron, stainless steel, carbon steel, glass, and the like.

Pressure is not critical in the reaction to convert nonaromatic hydrocarbons to maleic anhydride. The reaction may be conducted at atmospheric, superatmospheric, or subatmospheric pressures. It will generally be preferred, however, for practical reasons to conduct the reaction at or near atmospheric pressure. Generally, pressures from about $1.013 \times 10^2$ kPa-G (14.7 psig, 1 atm.) to about $1.38 \times 10^2$ kPa-G (20.0 psig) may be conveniently employed.

Maleic anhydride produced by using the process of the instant invention can be recovered by any means well known to those skilled in the art. For example, maleic anhdride can be recovered by direct condensation or by absorption in suitable media with subsequent separation and purification of the anhydride.

A large number of nonaromatic hydrocarbons having from four to 10 carbon atoms can be converted to maleic anhydride by using the catalyst prepared according to the instant process. It is only necessary that the hydrocarbon contain not less than four carbon atoms in a straight chain. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as an unbranched chain having at least four carbon atoms are present in the saturated hydrocarbon molecule.

Unsaturated hydrocarbons are also suitable for conversion to maleic anhydride using the catalyst prepared according to the instant process. Suitable unsaturated hydrocarbons include the butenes (1-butene and 2-butene), 1,3-butadiene, the pentenes, the hexenes, the heptenes, the octenes, the nonenes, the decenes, and mixtures of any of these, with or without the butenes, again, so long as the requisite unbranched C$_4$ hydrocarbon chain is present in the molecule.

Cyclic compounds, such as cyclopentane, cyclopentene, cyclohexane, or cyclohexene, are also satisfactory feed materials for conversion to maleic anhydride.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbon.

The principal product from the oxidation of the above-noted feed materials is maleic anhydride, although small amounts of citraconic anhydride (methylmaleic anhydride) may also be produced when the feedstock is a hydrocarbon containing more than four carbon atoms in a straight chain.

The following specific examples illustrating the best currently-known method of practicing this invention are described in detail in order to facilitate a clear understanding of the invention. It should be understood, however, that the detailed expositions of the application of the invention while indicating preferred embodiments, are given by way of illustration only and are not to be construed as limiting the invention since various changes and modification within the spirit of the invention will become apparent to those skilled in the art from this detailed description.

EXAMPLE 1

(a) Diphosphoric Acid

To a three-liter, round bottom flask equipped with a paddle stirrer was charged 276.6 g (2.84 moles) of 100.54% phosphoric acid ($H_3PO_4$) with 97.6 g (0.64 mole) of phosphorus oxytrichloride ($POCl_3$). The mixture was stirred and heated to 73° C. for three hours, during which period large amounts of hydrogen chloride (HCl) gas were evolved. Following this period, the reaction mass was heated to 105° C. for one hour and cooled to room temperature. The resulting liquid was allowed to stand at room temperature for four days, after which period, the liquid crystallized to form solid diphosphoric acid, $H_4P_2O_7$.

(b) Catalyst

A five-liter, round bottom flask fitted with a paddle stirrer, thermometer, heating mantle, and reflux condenser with water scrubber was charged with 3436 ml (4088.8 g, 41.45 moles) of concentrated (37%) hydrochloric acid and 295.0 g (1.62 moles) of high-purity vanadium pentoxide ($V_2O_5$). The mixture was heated to 103° C., at which temperature reflux was attained. When chlorine ($Cl_2$) gas was no longer evolved from the flask, a total of 2600 ml of solvent was removed from the reaction by distillation. To this concentrated $VOCl_2$ solution was added a solution of 303.1 g (1.78 moles) of $H_4P_2O_7$ [the entire mass from Section (a) above] in 590 ml of $H_2O$ (P/V atom mole of 1.05). This blue solution was held at 90° C. overnight. Thereafter a series of concentration/dilution (distillation/water addition) cycles was performed as follows:

| Cycle | Sol'n ml | Solv. Dist. ml | Solv. Dist. Fract. | H$_2$O Added, ml | H$_2$O Added/- Solv. Dist. |
|---|---|---|---|---|---|
| 1 | 1426 | 600 | 0.42 | 300 | 0.50 |
| 2 | 1126 | 600 | 0.53 | 300 | 0.50 |
| 3 | 826 | 325 | 0.39 | 300 | 0.92 |
| 4 | 801 | 400 | 0.50 | 1000 | 2.50 |

After cycle 2, a small quantity of crystals was observed, which amount visibly increased after the distillation step of cycle 4. The reaction mixture, which was quite thick at this point, was treated with one liter of water (final liquid/initial liquid volume ratio of 0.98), cooled to 70° C., and suction filtered. The filter cake was thoroughly washed with water and dried for 72 hours at 130° C. The granulated [−24 mesh (U.S. Standard Sieve Size)] powder was light blue in color (P/V atom ratio of 1.00). The dried, granulated precursor powder was mixed with one weight percent of powdered graphite and formed into 0.48-cm (0.1875-inch) cylinders (tablets) having an average (side) crush strength of 8.90 newtons (N, 2.00 lbs.). The tablets were calcined in air at 400° C. for six hours. The calcined catalyst was performance tested in a 2.54-cm (1-inch) inside diameter × 15.24-cm (6-inch) long tubular fixed-bed reactor at 1450 hr$^{-1}$ and 2600 hr$^{-1}$ space velocities and 1.5 mole percent n-butane-in-air. The parameters and results are tabulated in Tables 1 and 2.

EXAMPLE 2

(a) Diphosphoric Acid

To a two-liter, round bottom flask, equipped with a stainless steel paddle stirrer, was added 1000.0 g (11.17 moles) of 116% phosphoric acid ($H_3PO_4$) and 53.3 g (2.96 moles) of $H_2O$ at 25° C. The mixture was stirred while its temperature rose to 90° C. The solution (110.12% $H_3PO_4$) was cooled to 35° C. and 41.5 g (0.23 mole) of seed diphosphoric acid ($H_4P_2O_7$) crystals were added to the $H_3PO_4$. Stirring was continued for six hours until it was impossible to continue because of crystallization of the $H_4P_2O_7$. The semi-solid mass was kept at 22° C. overnight (approximately 16 hours). The resulting solid mass was chipped out of the flask and stored in a desiccator over Drierie ® (anhydrous calcium sulfate).

(b) Catalyst

The procedure described in Example 1 was repeated except that crystalline $H_4P_2O_7$ from Section (a) above was employed.

To a five-liter, round bottom flask fitted with a reflux condenser, paddle stirrer, exit gas water scrubber, thermometer and heating mantle was charged 3436 ml (4088.8 g, 41.45 moles) of concentrated (37%) hydrochloric acid and 295.0 g (1.62 moles) of high-purity $V_2O_5$. The mixture was heated to reflux and held at reflux for 18 hours. After this time, 2600 ml of distillate was removed at atmospheric pressure and a solution of 291.57 g (1.64 moles) of $H_4P_2O_7$ in 600 ml of water was added to the blue vanadium solution (P/V atom ratio of 1.01). A series of distillation/water addition cycles was then performed as follows:

| Cycle | Sol'n ml | Solv. Dist. ml | Solv. Dist. Fract. | H$_2$O Added, ml | H$_2$O Added/- Solv. Dist. |
|---|---|---|---|---|---|
| 1 | 1436 | 600 | 0.42 | 300 | 0.52 |
| 2 | 1136 | 350 | 0.31 | 300 | 0.86 |
| 3 | 1086 | 425 | 0.39 | 300 | 0.71 |
| 4 | 961 | 325 | 0.34 | 300 | 0.92 |
| 5 | 936 | 300 | 0.32 | 1300 | 4.33 |
| 6 | 1936 | 1400 | 0.72 | 150 | 0.11 |

After these six cycles, the reaction mixture was a thick blue slurry, with a final liquid/initial liquid volume ratio of 0.48. The mixture was cooled to room temperature and suction filtered. The filter cake was thoroughly washed with water until the filtrate was clear, dried overnight at 130° C., and granulated to give a blue granular powder. The dried precursor powder was mixed with one weight percent of powdered graphite and formed into 0.48-cm (0.1875-inch) cylinders (tablets). The tablets were calcined in air at 400° C. for six hours to yield the catalyst having a P/V atom ratio of 0.99. The catalyst was performance tested as described in Example 1. The parameters and results are tabulated in Tables 1 and 2.

EXAMPLE 3

A twelve-liter, round bottom flask, fitted with paddle stirrer, thermometer, two-zone heating mantle and reflux condenser (attached to a water scrubbing column), was charged with 6872 ml (8177.7 g, 82.90 moles) of concentrated (37%) hydrochloric acid and 590.0 g (3.24 moles) of high-purity $V_2O_5$. The mixture was heated from approximately 35° C. to reflux temperature (102°–104° C.) Reflux was maintained for 20 hours. During the heating/reflux time, the orange mixture first turned to a dark red solution, then gradually to a dark blue solution. After the hold period, a total of 5200 ml of solvent was distilled from the reaction solution. The solution was cooled to 50° C. and a mixture of 583.14 g (3.28 moles) of crystalline $H_4P_2O_7$ (from seeded crystallization of 110.12% $H_3PO_4$) in 1200 ml of water was added. The reaction mixture was heated to reflux temperature. Thereafter, a series of distillation/water addition cycles was performed as follows:

| Cycle | Sol'n ml | Solv. Dist. ml | Solv. Dist. Fract. | H₂O Added, ml | H₂O Added/- Solv. Dist. |
|---|---|---|---|---|---|
| 1 | 2872 | 1200 | 0.42 | 600 | 0.50 |
| 2 | 2272 | 700 | 0.31 | 600 | 0.86 |
| 3 | 2172 | 850 | 0.39 | 600 | 0.71 |
| 4 | 1922 | 700 | 0.36 | 600 | 0.86 |
| 5 | 1822 | 800 | 0.44 | 1000 | 1.25 |
| 6 | 2022 | 1650 | 0.82 | 500 | 0.30 |

A total of 11,972 ml of liquid was added to the flask. A total of 11,100 ml of liquid was distilled out to give a final liquid/initial liquid volume ratio of 0.30.

Crystallization of a blue product was observed after the distillation step of cycle 3. The amount of precipitate increased throughout the repetitive cycles. After the final cycle (cycle 6), the blue slurry was cooled to room temperature and suction filtered. The filter cake was thoroughly washed with water, dried at 130° C. for 60 hours and granulated [−25 mesh (U.S. Standard Sieve Size)] to yield a blue powder having a P/V mole ratio of 1.01. The dried catalyst precursor powder was mixed with one weight percent of powdered graphite and formed into 0.48-cm (0.1875-inch) cylinders (tablets) having an average (side) crush strength of 22.25 N (5.00 lbs). The tablets were calcined in air at 400° C. for six hours to yield the catalyst having a P/V atom ratio of 1.00. The catalyst was performance tested as described in Example 1 except that a 2.54-cm (1 inch) inside diameter×121.91-cm (4 foot) tubular fixed-bed reactor was employed. The parameters and results are tabulated in Tables 1 and 2.

EXAMPLE 4

A three-liter, round bottom flask fitted with a paddle stirrer, thermometer, addition funnel, reflux condenser, water scrubber, and heating mantle was charged with 2000 ml (2380.0 g, 24.13 moles) of concentrated (37%) aqueous HCl, 100 ml of isobutyl alcohol, and 162.2 g (0.89 mole) of high-purity $V_2O_5$. The mixture was heated, with stirring, to reflux and maintained at reflux for one hour. The solution was then distilled at atmospheric pressure to remove 1400 ml of distillate. To the residual solution was added 160.35 g (0.90 mole) of crystalline $H_4P_2O_7$ (from seeded crystallization of 110.12% $H_4PO_4$) dissolved in 100 ml of concentrated (37%) aqueous HCl. An additional 50 ml of concentrated aqueous HCl was used to rinse residual $H_4P_2O_7$ into the reaction flask. A series of distillation/water addition cycles was then performed as follows:

| Cycle | Sol'n ml | Solv. Dist. ml | Solv. Dist. Fract. | H₂O Added, ml | H₂O Added/- Solv. Dist. |
|---|---|---|---|---|---|
| 1 | 850 | 350 | 0.41 | 100 | 0.29 |
| 2 | 600 | 125 | 0.21 | 100 | 0.80 |
| 3 | 575 | 100 | 0.17 | 100 | 1.00 |
| 4 | 575 | 100 | 0.17 | 200 | 2.00 |
| 5 | 675 | 150 | 0.22 | 1000 | 6.67 |

After cycle 3, a small quantity of crystals was observed, which amount visibly increased after cycle 4. After cycle 5, the mixture, having a final liquid/initial liquid volume ratio of 1.79, was cooled to 70° C. and suction filtered. The filter cake was washed with 200 ml of deionized water, filtered, dried overnight in air at 130° C., and granulated [−25 mesh (U.S. Standard Sieve Size)] to yield a blue granular powder. The dry powder was formed into tablets and calcined as described in Example 3. The calcined tablets were performance tested at 1450 hr$^{-1}$ as described in Example 1. The parameters and results are tabulated in Tables 1 and 2.

EXAMPLES 5–8 (Comparative)

Examples 5–8 illustrate the criticality of the combination of crystalline diphosphoric acid and the controlled crystallization procedure to produce superior catalysts.

| Example | Critical Feature Present | |
|---|---|---|
| | H₄P₂O₇ | Controlled Crystallization |
| 5 | No | Yes |
| 6 | Yes | No |
| 7 | Yes | No |
| 8 | No | Yes |

EXAMPLE 5 (Comparative)

A three-liter, round bottom flask fitted as described in Example 4 was charged with 2000 ml (2380.0 g, 24.13 moles) of concentrated (37%) aqueous HCl, 100 ml of isobutyl alcohol, and 162.2 g (0.89 mole) of high-purity $V_2O_5$. The mixture was heated, with stirring, to reflux and maintained at reflux for one hour. The solution was then distilled at atmospheric pressure to remove 1400 ml of distillate. To the residual solution was added 122 ml (206.5 g, 1.80 moles) of 85.5% $H_3PO_4$. Thereafter, a series of distillation/water addition cycles was performed to give a final liquid/initial liquid volume ratio of 1.92.

| Cycle | Sol'n ml | Solv. Dist. ml | Solv. Dist. Fract. | H₂O Added, ml | H₂O Added/- Solv. Dist. |
|---|---|---|---|---|---|
| 1 | 822 | 155 | 0.18 | 100 | 0.65 |
| 2 | 767 | 160 | 0.21 | 100 | 0.63 |
| 3 | 707 | 125 | 0.18 | 100 | 0.80 |
| 4 | 682 | 125 | 0.18 | 200 | 1.60 |
| 5 | 757 | 200 | 0.26 | 200 | 1.00 |
| 6 | 757 | 200 | 0.26 | 500 | 2.50 |
| 7 | 1057 | 480 | 0.45 | 500 | 1.04 |
| 8 | 1077 | 500 | 0.46 | 500 | 1.00 |
| 9 | 1077 | 500 | 0.46 | 1000 | 2.00 |

A small amount of crystals appeared during cycle 4 which visibly increased following each cycle through cycle 8. After cycle 9, the mixture was cooled to 70° C. and suction filtered. The filter cake was thoroughly washed with water, dried overnight in air at 130° C., and granulated [−18 mesh (U.S. Standard Sieve Size)] to yield a blue granular powder. The dry powder was spheroidized on a 40.64-cm (16-inch) pan pelletizer with water spray. The spheres were dried overnight (approximately 16 hours) at 130° C. and screened to yield spheres having a diameter from about 0.48 cm to about 0.67 cm. The dry spheres were calcined in air at 400° C. for six hours. The calcined spheres were performance tested at 1450 hr$^{-1}$ as described in Example 1. The parameters and results are tabulated in Tables 1 and 2.

EXAMPLE 6 (Comparative)

A twelve-liter, round bottom flask, fitted as described in Example 3 was charged with 7570 ml (9008.3 g, 91.32 moles) of concentrated (37%) aqueous HCl and 644.0 g (3.54 moles) of high-purity $V_2O_5$. The mixture was heated to reflux and refluxed for about 18 hours. After the reflux period, a total of 6100 ml of solvent was distilled from the reaction solution. The residual blue syrup was cooled to room temperature and quantitatively transferred to a five-liter beaker with 1500 ml of water. To the resulting solution was added 645.98 g (3.63 moles) of crystal-line $H_4P_2O_7$ (from seeded crystallization) of 110.12% $H_3PO_4$) at a rate sufficient to maintain the temperature below 45° C. (P/V atom ratio of 1.025). The blue solution was heated at 70° C. overnight (approximately 16 hours) and concentrated at its boiling point to a thick slurry (near dryness). The slurry was taken up in 1000 ml of water and filtered. The filter cake was washed with water until the filtrate was clear, dried at 130° C., and granulated [−25 mesh (U.S. Standard Sieve Size)] to yield a blue granular powder. The dry powder was mixed with 1.5 weight percent of powdered graphite and formed into 0.48-cm (0.1875-inch) cylinders (tablets). The tablets were tray calcined in air at 400° C. for six hours to yield the catalyst having a P/V atom ratio of 1.00. The catalyst was performance tested as described in Example 1. The parameters and results are tabulated in Tables 1 and 2.

EXAMPLE 7 (Comparative)

A three-liter, round bottom flask fitted with a paddle stirrer, thermometer addition funnel, reflux condenser, water scrubber, and heating mantle was charged with 1750 ml (2082.5 g, 21.11 moles) of 12 N (37%) aqueous HCl and 1622.5 g (8.91 moles) of $V_2O_5$. The mixture was stirred at a moderate rate to maintain the solids in suspension and heated to reflux. The reflux temperature was maintained for 20 hours to yield a blue solution. The solution was distilled to remove 13,125 ml of distillate and treated with 1667.1 g (9.37 moles) of $H_4P_2O_7$ (from seeded crystallization of 110.12% $H_3PO_4$) and 324.0 g of $H_2O$ (equivalent to 85% $H_3PO_4$. The mixture was distilled to remove an additional 2000 ml of distillate. The residual slurry was dried at 130° C. to yield a blue product [−24 mesh (U.S. Standard Sieve Size)]. The dry powder was spheroidized on a 40.64-cm (16-inch) pan pelletizer with water spray. The spheres were dried overnight (approximately 16 hours) at 130° C. and screened to yield spheres having a diameter from about 0.48 cm to about 0.67 cm. The dry spheres were calcined in air at 400° for six hours. The calcined spheres were performance tested as described in Example 3. The parameters and results are tabulated in Tables 1 and 2.

EXAMPLE 8 (Comparative)

A three-liter, round bottom flask fitted as described in Example 3 was charged with 1743 ml (2074.4 g, 21.03 moles) of concentrated (37%) aqueous HCl and 162.2 g (0.89 mole) of high-purity $V_2O_5$. The mixture was heated to reflux and maintained at reflux temperature, with stirring, for two hours. The resulting solution was distilled to remove 1410 ml of colorless distillate. The remaining solution was reacted with 122 ml (206.5 g, 1.80 moles) of 85.5% $H_3PO_4$ and 200 ml of water. Thereafter, a series of distillation/water addition cycles was performed as follows:

| Cycle | Sol'n ml | Solv. ($H_2O$/HCl) ml | Fract. | $H_2O$ Added, ml | $H_2O$ Added/- Solv. Dist. |
|---|---|---|---|---|---|
| 1 | 655 | 205 | 0.31 | 200 | 0.98 |
| 2 | 650 | 250 | 0.38 | 200 | 0.80 |
| 3 | 600 | 100 | 0.17 | 200 | 2.00 |

After cycle 3, the mixture, having a final liquid/initial liquid volume ratio was 1.07, was cooled to 70° C. and suction filtered. The filter cake was resuspended in 1000 ml of water, filtered, and dried overnight (approximately 16 hours) at 130° C. to yield a blue powder [−24 mesh (U.S. Standard Sieve Size)] having a P/V atom ratio of 0.99. The dry powder was mixed with one weight percent of powdered graphite and formed into 0.48-cm (0.1875-inch) cylinders having an average crush strength of 22.25 N (5.00 lbs). The tablets were calcined in air at 400° C. for six hours. The calcined tablets were performance tested at 1450 hr$^{-1}$ as described in Example 1. The parameters and results are tabulated in Tables 1 and 2.

EXAMPLE 9 (Comparative)

This Example illustrates a typical prior art catalyst prepared from 85 percent orthophosphoric acid and a concentrating/water dilution technique. The catalyst was prepared according to the procedure described in Example 1 of U.S. Pat. No. 4,085,122.

To a five-liter, round bottom flask fitted with a mechanical stirrer, condenser, and an HCl gas scrubber was charged 400.0 g (2.20 moles) of high-purity $V_2O_5$ and 2712 ml (3200.0 g, 32.44 moles) of concentrated (37%) aqueous HCl. The suspension was heated to 100°±2° C. in 80±20 minutes, and was held at this temperature for two hours, during which period chlorine ($Cl_2$) gas was evolved. The resulting deep blue solution was cooled slightly and 39.19 g (0.31 mole) of oxalic acid dihydrate [($COOH_2.2H_2O$], 325 ml (548.0 g, 4.75 moles) of 85% $H_3PO_4$, and 280 ml of deionized water were added slowly (P/V atom ratio of 1.08). The flask was set up for distillation and two cycles of distillation/water addition were performed to give a final liquid/initial liquid volume ratio of 0.42.

| Cycle | Sol'n ml | Solv. Dist. ml | Fract. | $H_2O$ Added | $H_2O$ Added/- Solv. Dist. |
|---|---|---|---|---|---|
| 1 | 3317 | 2418 | 0.73 | 500 | 0.21 |
| 2 | 1399 | 800 | 0.57 | 800 | 1.00 |

The resulting precipitate was collected by filtration, washed with four 250-ml portions of deionized $H_2O$, and air dried. The dried material was suspended in 1000 ml of deionized water, boiled at 100° C. for two hours, filtered, washed, air dried, and heated overnight (approximately 16 hours) at 120° C. in a forced draft oven. The granulated powder was mixed with one weight percent of powdered graphite and formed into 0.48-cm (0.1875-inch) tablets and calcined in air at 400° C. for six hours. The catalyst was performance tested as described in Example 1. The parameters and results are tabulated in Tables 1 and 2.

was cooled to 70° C. and transferred to a porcelain dish and dried in an oven at 130° C. for about 50 hours. The dry material was then heated in air at 365° C. for two hours. The tablets were calcined in dry air for six hours at 400° C. The catalyst was performance tested as described in Example 1. The parameters and results are tabulated in Tables 1 and 2.

TABLE 1

| EX. | NO. | EMPIRICAL FORMULA[1] | FORM (SIZE, cm) | P/V ATOM RATIO | $V^{+4}/V^{t2}$ | AVERAGE VANADIUM VALENCE | POROSITY % | MEAN PORE DIAMETER $\mu m$ | TOTAL PORE VOLUME cc/g | BET SURFACE AREA $m^2/g$ |
|---|---|---|---|---|---|---|---|---|---|---|
| 1 | 1 | $P_{1.0}V_{1.0}O_x$ | Tablets (0.48) | 1.00 | 19.93 | 4.80 | 35.20 | 0.20 | 0.22 | 17.00 |
| 2 | 2 | $P_{0.99}V_{1.0}O_x$ | " | 0.99 | 17.21 | 4.83 | 38.65 | 0.11 | 0.16 | 8.30 |
| 3 | 3 | $P_{1.0}V_{1.0}O_x$ | " | 1.00 | 18.44 | 4.82 | 32.45 | 0.15 | 0.17 | 8.50 |
| 4[3] | 4 | $P_{1.03}V_{1.0}O_x$ | " | 1.03 | 27.46 | 4.73 | 35.98 | 0.18 | 0.21 | — |
| 5[3,4] | 5 | $P_{1.02}V_{1.0}O_x$ | Spheres (0.48–0.67) | 1.02 | 24.67 | 4.75 | 27.94 | 0.13 | 0.15 | — |
| 6[4] | 6 | $P_{1.04}V_{1.0}O_x$ | Tablets (0.48) | 1.04[5] | 26.42 | 4.74 | 33.71 | 0.16 | 0.18 | 5.90 |
| 7[4] | 7 | $P_{1.05}V_{1.0}O_x$ | Spheres (0.48–0.67) | 1.05 | 30.16 | 4.70 | 41.37 | 0.19 | 0.26 | 3.50 |
| 8[4] | 8 | $P_{0.99}V_{1.0}O_x$ | Tablets (0.48) | 0.99 | 26.51 | 4.74 | — | — | — | — |
| 9[4] | 9 | $P_{1.04}V_{1.0}O_x$ | " | 1.04[6] | 30.20 | 4.70 | 53.20 | 0.16 | 0.29 | — |
| 10[4] | 10 | $P_{1.05}V_{1.0}O_x$ | " | 1.05 | 28.10 | 4.72 | 31.30 | 0.12 | 0.18 | 4.20 |

[1]Subscript x is a number taken to satisfy the valence requirements of phosphorus and vanadium.
[2]$V^t$ represents total vanadium.
[3]The aqueous medium contained added isobutyl alcohol.
[4]Comparative example.
[5]Apparently due to a greater relative loss of vanadium than phophorus during the recovery of the crystalline catalyst precursor since the charged P/V atom ratio was 1.025.
[6]The analyzed P/V atom ratio for the filtered catalyst was 1.04 rather than 1.08 as claimed in Example 1 of U.S. Pat. No. 4,085,122.

TABLE 2

| CATALYST NO. | CATALYST REACTOR CHARGE DENSITY $(kg/m^3) \times 10^3$ | SPACE VELOCITY $hr^{-1}$ | n-BUTANE mole % | TEMPERATURE, °C. BATH | TEMPERATURE, °C. REACTION | CONV. mole % | SEL. mole % | YIELD mole % |
|---|---|---|---|---|---|---|---|---|
| 1 | 0.94 | 1450 | 1.5 | 382 | 408 | 80.4 | 70.3 | 56.5 |
| " | " | 2600 | 1.5 | 397 | 436 | 72.1 | 65.8 | 47.4 |
| 2 | 0.96 | 1450 | 1.5 | 387 | 414 | 80.0 | 70.2 | 56.1 |
| " | " | 2600 | 1.5 | 399 | 439 | 71.5 | 66.1 | 47.2 |
| 3 | 1.17 | 1450 | 1.5 | 390 | 436 | 80.1 | 71.3 | 57.1 |
| " | " | 2600 | 1.5 | 413 | 460 | 70.6 | 67.6 | 47.7 |
| 4 | 0.96 | 1450 | 1.5 | 388 | 419 | 79.3 | 69.8 | 55.4 |
| " | " | 2600 | 1.5 | 404 | 455 | 71.2 | 64.4 | 45.9 |
| 5[1] | 0.98 | 1450 | 1.5 | 402 | 438 | 78.1 | 65.5 | 50.7 |
| 6[1] | 1.02 | 1450 | 1.5 | 402 | 423 | 80.0 | 67.0 | 53.5 |
| " | " | 2600 | 1.5 | 414 | 450 | 71.7 | 61.1 | 43.8 |
| 7[1] | 0.77 | 1450 | 1.5 | 432 | 470 | 80.4 | 62.0 | 49.8 |
| 8[1] | 0.98 | 1450 | 1.5 | 399 | 433 | 79.5 | 65.5 | 52.0 |
| " | " | 2600 | 1.5 | 416 | 463 | 71.2 | 60.3 | 42.9 |
| 9[1] | 0.93 | 1450 | 1.5 | 390 | 424 | 79.1 | 67.6 | 53.5 |
| " | " | 2600 | 2.0 | 398 | 483 | 64.4 | 60.3 | 38.8 |
| 10[1] | 0.92 | 1450 | 1.5 | 407 | 431 | 79.0 | 62.1 | 49.1 |

[1]Comparative catalyst.

tabulated in Tables 1 and 2.

EXAMPLE 10 (Comparative)

This Example illustrates an early prior art catalyst prepared in an aqueous medium using hydrochloric acid as the reducing agent. The catalyst was prepared according to the procedure described in Example 2 of U.S. Pat. No. 3,293,268.

A three-liter, round bottom flask fitted with a paddle stirrer, thermometer, addition funnel, reflux condenser, water scrubber, and heating mantle was charged with 1750 ml (2082.5 ml, 21.11 moles) of 12 N hydrochloric acid (HCl) and 134.4 g (0.74 mole) of $V_2O_5$. The mixture was stirred at a moderate rate to maintain the solids in suspension and heated to 90° C. over a two-hour period to give a blue solution. To this solution was added, over a 20-minute period, 105 ml (177.6 g, 1.55 moles) of 85.5% phosphoric acid (P/V atom ratio of 1.05). During the phosphoric acid addition, the reaction temperature did not exceed 91° C. The reaction mixture Comparison of the yields of maleic anhydride obtained with catalysts 1–4 with those obtained with comparative catalysts 5–10 clearly demonstrates the advantages of the instant process to prepare catalysts in aqueous media in that the yields are significantly higher for catalysts 1–4 when compared with comparative catalysts 5–10.

Thus, it is apparent that there has been provided, in accordance with the present invention, a process that fully satisfies the objects and advantages set forth hereinabove. While the invention has been described with respect to various specific examples and embodiments thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the production of maleic anhydride by the oxidation of a nonaromatic hydrocarbon having at least four carbon atoms in a straight chain with molecular oxygen or a molecular oxygen containing gas in the vapor phase at a temperature from abut 300° C. to about 600° C. in the presence of a phosphorus-vanadium mixed oxide catalyst wherein the catalyst is prepared by:
   (a) contacting a tetravalent vanadium compound, dissolved in an aqueous, non-oxidizing acid medium, with crystalline diphosphoric acid to form a phosphorus-vanadium mixed oxide catalyst precursor;
   (b) crystallizing the catalyst precursor from the catalyst precursor aqueous solution in a controlled manner involving at least three cycles of concentrating/diluting wherein a fraction of the liquid from about 0.15 to about 0.85 is removed during the concentrating step and water is added during the diluting step in an amount sufficient to provide a water added/solvent removed volume ratio from about 0.10 to about 10.0, with the proviso that the final liquid/initial liquid volume ratio is from about 0.20 to about 2.0;
   (c) recovering the catalyst precursor crystals;
   (d) drying the catalyst precursor;
   (e) forming the dried catalyst precursor into structures, and
   (f) calcining the catalyst precursor structures at a temperature from about 300° C. to about 600° C.

2. The process of claim 1 wherein the catalyst has a phosphorus/vanadium atom ratio from about 0.5 to about 2.0.

3. The process of claim 2 wherein the catalyst has a phosphorus/vanadium atom ratio from about 0.95 to about 1.2.

4. The process of claim 1 wherein the tetravalent vanadium compound is selected from the group consisting of the halides, oxides, and oxyhalides of vanadium.

5. The process of claim 4 wherein the tetravalent vanadium compound is a vanadium oxyhalide.

6. The process of claim 5 wherein the vanadium oxyhalide is vanadium oxydichloride.

7. The process of claim 1 wherein the tetravalent vanadium compound is formed by the in situ reduction of a pentavalent vanadium compound.

8. The process of claim 7 wherein the pentavalent vanadium compound is selected from the group consisting of halides, oxides, and oxyhalides of vanadium.

9. The process of claim 8 wherein the pentavalent vanadium compound is a vanadium oxide.

10. The process of claim 9 wherein the vanadium oxide is vanadium pentoxide.

11. The process of claim 1 wherein the aqueous, non-oxidizing acid medium is concentrated hydrochloric acid.

12. The process of claim 1 wherein the catalyst precursor crystals are recovered by filtration.

13. The process of claim 1 wherein the catalyst precursor structures are tablets.

14. The process of claim 1 wherein the catalyst precursor calcination temperature is about 400° C.

15. The process of claim 1 wherein the nonaromatic hydrocarbon is a saturated hydrocarbon.

16. The process of claim 15 wherein the saturated hydrocarbon is n-butane.

17. The process of claim 1 wherein the molecular oxygen-containing gas is air.

18. The process of claim 17 wherein the nonaromatic hydrocarbon-in-air concentratation is from about one mole percent to about 10 mole percent.

19. The process of claim 18 wherein the nonaromatic hydrocarbon-in-air concentration is about 1.5 mole percent.

20. The process of claim 1 wherein the oxidation of the nonaromatic hydrocarbon with molecular oxygen or a molecular oxygen-containing gas is carried out at a temperature from about 325° C. to about 425° C.

21. The process of claim 1 wherein the phosphorus-vanadium mixed oxide catalyst is employed in a fixed bed.

22. A process for the production of maleic anhydride by the oxidation of n-butane with molecular oxygen or a molecular oxygen containing gas in the vapor phase at a temperature from about 325° C. to about 425° C. in the presence of a phosphorus-vanadium mixed oxide catalyst having a phosphorus/vanadium atom ratio of about 0.95 to about 1.2 wherein the catalyst is prepared by:
   (a) contacting vanadium oxydichloride, dissolved in aqueous hydrochloric acid, with crystalline diphosphoric acid to form a phosphorus-vanadium mixed oxide catalyst precursor;
   (b) crystallizing the catalyst precursor from the catalyst precursor aqueous solution in a controlled manner involving at least three cycles of concentrating/diluting wherein a fraction of the liquid from about 0.15 to about 0.85 is removed during the concentrating step and water is added during the diluting step in an amount sufficient to provide a water added/solvent removed volume ratio from about 0.10 to about 10.0, with the proviso that the final liquid/initial liquid volume ratio is from about 0.20 to about 2.0;
   (c) filtering the catalyst precursor crystals from the water-diluted catalyst precursor mixture;
   (d) drying the catalyst precursor;
   (e) forming the catalyst precursor into structures; and
   (f) calcining the catalyst precursor structures at a temperature from about 400° C. to about 500° C. for a period of time from about four hours to about eight hours.

23. The process of claim 22 wherein the molecular oxygen-containing gas is air.

24. The process of claim 23 wherein the n-butane-in-air concentration is from about one mole percent to about 10 mole percent.

25. The process of claim 24 wherein n-butane-in-air concentration is about 1.5 mole percent.

26. The process of claim 22 wherein the phosphorus-vanadium mixed oxide catalyst is employed in a fixed bed.

* * * * *